United States Patent [19]

Alvarez-Jacinto

[11] Patent Number: 5,052,374
[45] Date of Patent: Oct. 1, 1991

[54] HERNIA RETRACTOR

[76] Inventor: Manuel Alvarez-Jacinto, 701 NW. 57 Ave., Suite 350, Miami, Fla. 33126

[21] Appl. No.: 563,577

[22] Filed: Aug. 6, 1990

[51] Int. Cl.$^5$ ............................................. A61B 17/02
[52] U.S. Cl. ................................................. 128/20
[58] Field of Search ................................. 128/17, 20; 606/205–209; 269/328

[56] References Cited

U.S. PATENT DOCUMENTS

| | | | |
|---|---|---|---|
| 2,070,670 | 2/1937 | Marshall | 128/20 |
| 2,586,488 | 2/1952 | Smith | 128/20 |
| 2,702,590 | 2/1955 | Debeh | 128/20 |
| 3,749,088 | 7/1973 | Kohlmann | 128/20 |
| 3,998,217 | 12/1976 | Trumbull et al. | 128/20 |
| 4,010,741 | 3/1977 | Kohlmann | 128/20 |
| 4,051,844 | 10/1977 | Chialli | 128/20 |
| 4,467,791 | 8/1984 | Cabrera et al. | 128/20 |
| 4,605,990 | 9/1984 | Wilder et al. | 128/20 |

FOREIGN PATENT DOCUMENTS 585549  3/1977  Switzerland ........................... 128/20

Primary Examiner—Edward M. Coven
Assistant Examiner—Mark S. Graham

[57] ABSTRACT

A retractor for operating on hernias comprising a frame member and several gripping, hook and elongated gripping instruments that are removably mounted to the frame. Each instrument includes a mounting assembly that permits the rigid locking of the elongated portion of the instrument in place with respect to the mounting assembly so that the tissue or body part being pulled is maintained out of the area being operated on. The mounting assemblies are removably and pivotally mounted to one of several openings positions around the periphery of the frame assembly so that the instruments can be directed in any suitable angle.

6 Claims, 4 Drawing Sheets

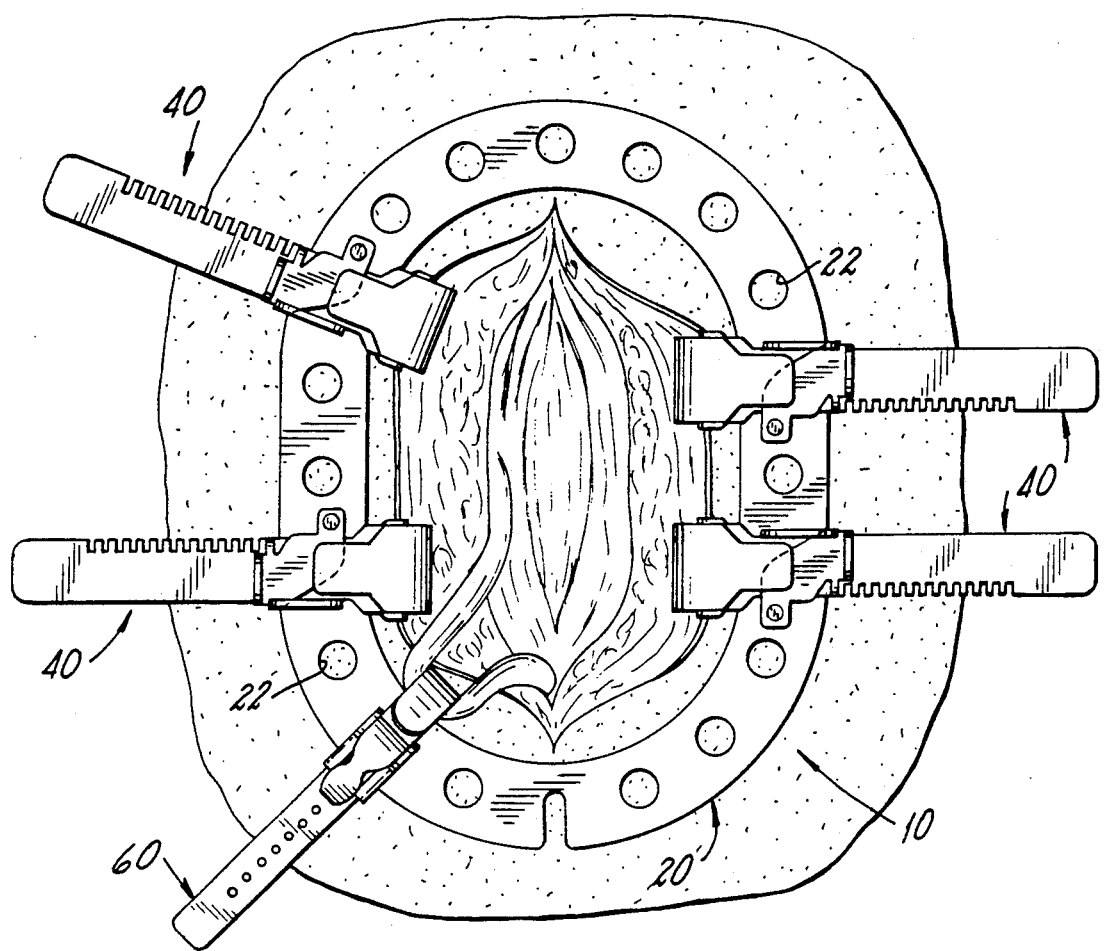
FIG - 1 -
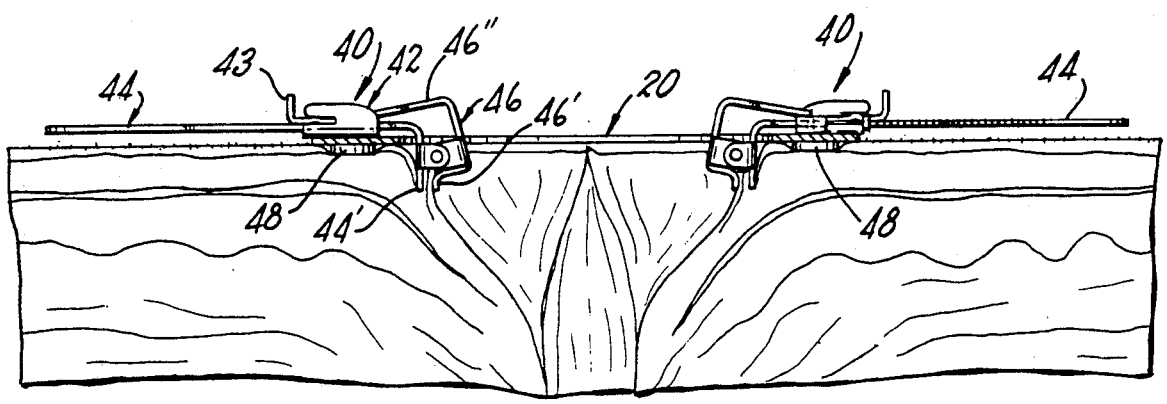
FIG - 2 -

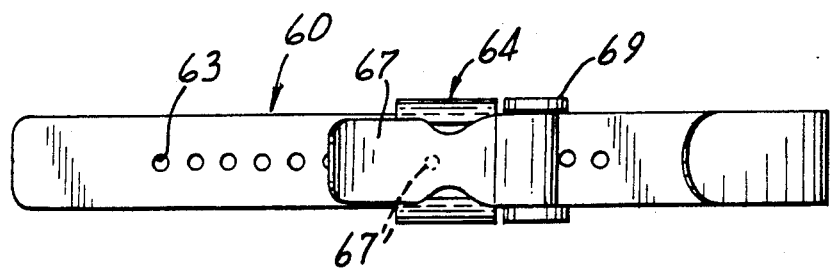
FIG-3-
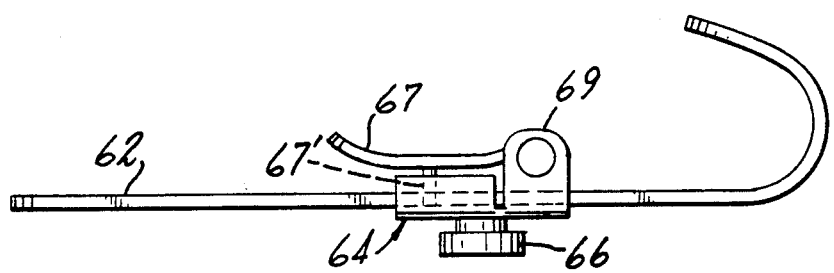
FIG-4-
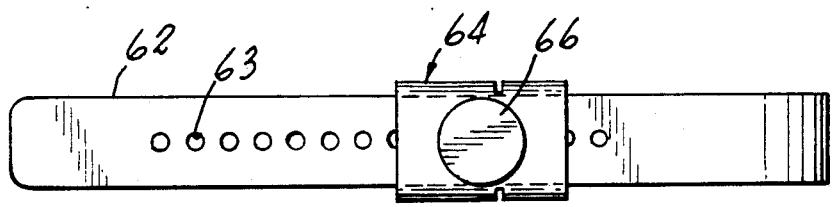
FIG-5-
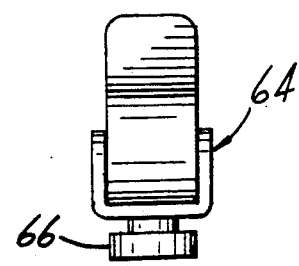
FIG-6-

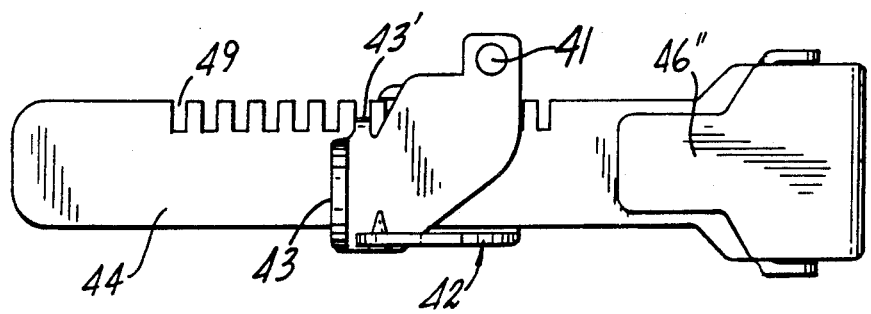
FIG. 7.
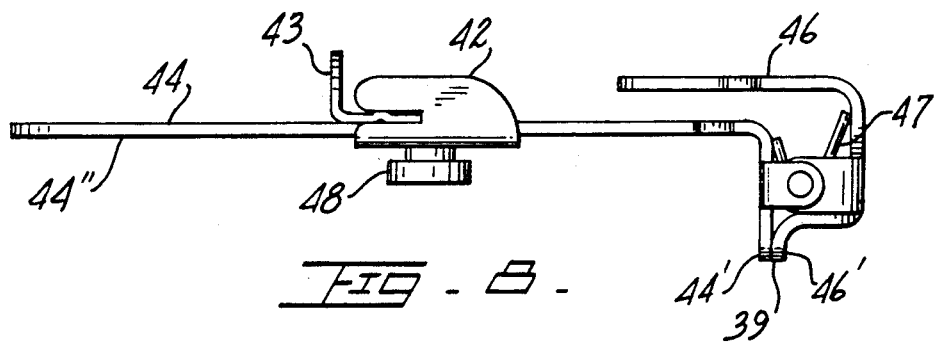
FIG. 8.
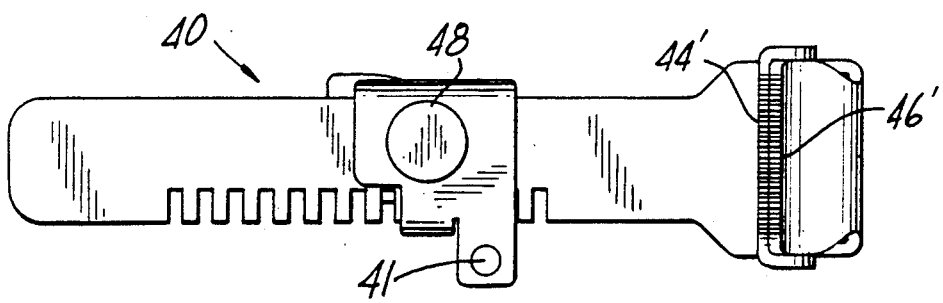
FIG. 9.
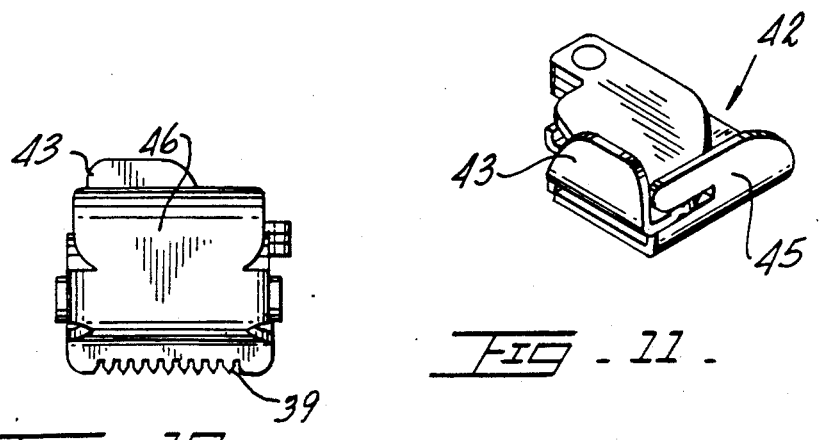
FIG. 10.
FIG. 11.

HERNIA RETRACTOR

BACKGROUND OF THE INVENTION

1. Field of the Invention.

The present invention relates to surgical retractors, and more particularly, to such retractors used in hernia operations.

2. Description of the Related Art.

A number of retractors have been design in the past for deep abdominal operations. However, these devices are not practical for the more superficial hernia operations requiring the assistance of at least one additional person to aid in the separation of the different tissues.

Applicant believes that the closest reference corresponds to U.S. Pat. No. 3,749,088 issued to Kohlmann. However, it differs from the present invention because being designed for deep surgery it lacks the efficient features of the present invention for hernia operations that are more superficial and require retracting shallow tissues. In particular, one of the limitations of this invention is that the retracting or pulling action on the flesh can only be accomplished radially outwardly from the area being operated. Retractor arm 8 does not pivot at the point where it is radially slidably mounted to frame means 2.

Another abdominal retractor with the same limitations is described in U.S. Pat. No. 4,010,741 issued also to Kohlmann.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a surgical retractor for hernia operations that can be readily used and applied to a patient by the surgeon without requiring additional help.

It is another object of this present invention to provide a retractor that includes a number of removable gripping instruments and hook instruments that can be firmly and readily assembled around the periphery of the area being operated.

It is still another object of this present invention to provide a device that can be readily and efficiently operated even under slippery conditions associated with surgical operations.

It is yet another object of this present invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents a top view of the present invention showing four gripping instruments used on a patient and one hook instrument retracting a layer of skin away from the area being worked on.

FIG. 2 shows a side cross-sectional view of the representation of FIG. 1.

FIG. 3 illustrates a top view of one of the gripping instruments used in this invention.

FIG. 4 is a side elevational view of the gripping instrument represented in FIG. 3.

FIG. 5 is a bottom view of the gripping instrument represented in FIGS. 3 and 4.

FIG. 6 is an end view of the gripping instrument represented in the previous three figures.

FIG. 7 shows a top view of the hook instrument.

FIG. 8 is a side elevational view of the hook instrument shown in FIG. 7.

FIG. 9 is a bottom view of the hook instrument represented in FIGS. 7 and 8.

FIG. 10 is an end view of the hook instrument shown in the previous three figures.

FIG. 11 illustrates an isometric view of the mounting assembly used in the preferred embodiment with the gripping instruments.

DETAILED DESCRIPTION OF THE PREFERRED EMBODIMENT

Figure 12:
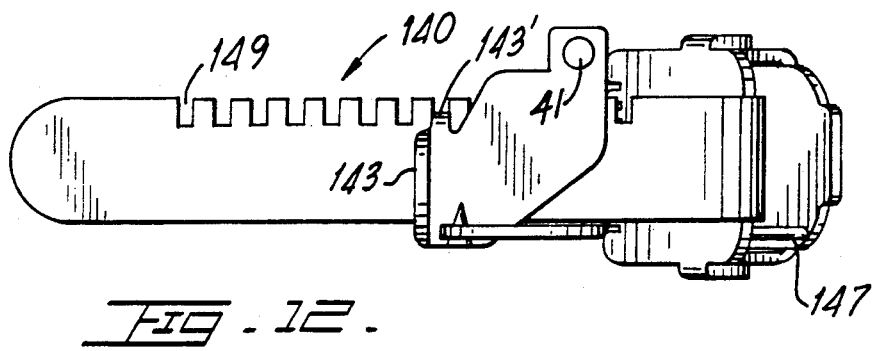
FIG. 12 represents a top view of an elongated gripping instruments utilized in the present invention to pull and retain deeper tissues.

Referring now to FIG. 1, where the present invention is generally referred to with numeral 10, it can be observed that it basically includes frame assembly 20 which has substantially an elliptical shape and being flat with several openings 22 all around it. A number of gripping instruments 40 and one hook instrument 60 are removably mounted to frame assembly 20 on openings 22.

In FIG. 2, a side elevational cross-sectional view showing two gripping instruments 40 holding and retracting flesh layers away from the area being operated. Gripping instruments 40 include mounting assembly 42 that is removably mounted to frame assembly 20, and more particularly, through opening 22. Lower jaw L-shaped member 44 co-acts with smaller L-shaped upper jaw member 46 to form two jaws that are urged against each other by spring member 47 and thereby facilitating the effective grabbing of tissues, specially, in the characteristically slippery environment in which it is used. This is particularly important in relatively superficial operations, such as hernia operations. To separate jaw ends 44' from 46', a user presses on surface 46" with sufficient force to overcome the action of spring member 47 which can be best seen in FIG. 8. Serrations 39 are provided as terminations for ends 44' and 46' in order to ensure the effective gripping of the tissues being pulled away.

Headed pin 48 extends downwardly from mounting assembly 42 and it has such cooperative dimensions to permit its insertion through opening 22. Mounting assembly 42 is removably and pivotally mounted to frame assembly 20 so that when gripping instrument is used to retract or pull a tissue, the latter can be directed in any desired angle. Mounting assembly 42 is provided with a locking mechanism that includes latching member 43 and anchor member 45 that are pivotally mounted to each other at 41. Latching member 43 includes locking pin 43' that locks lower jaw member 44 in place with respect to mounting assembly 42. Member 44 includes several cut-outs 49 at end 44" that receive locking pin 43'. Member 44 slides radially outwardly from the area being operated on but it is also permitted some angular flexibility so that it can retract tissues and things at an angle from a perpendicular line to the periphery of the frame. A surgeon can readily mount any one gripping instrument 40 at any one of the openings 22 and reach on to grab an edge of a layer of skin that is subsequently pulled outwardly and kept locked in place.

Hook instrument 60 includes elongated and flat hook member 62 and hook mounting assembly 64, as can be best seen from FIGS. 3 through 6. Headed pin 66 extends downwardly and it has such cooperative dimensions to permit its insertion through opening 22. Lever member 67 is hingedly mounted to hook mounting assembly 64 at 69. Lever member 67 includes locking pin 67' that cooperatively acts with holes 63 to lock hook member 62 in place.

Figure 13:
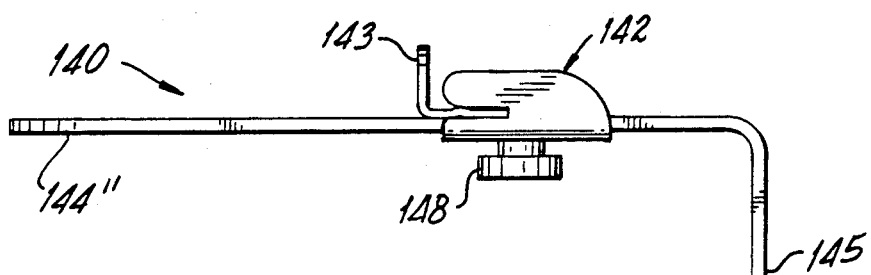
FIG. 13 shows a side view of the elongated gripping instrument represented in FIG. 12.
Figure 14:
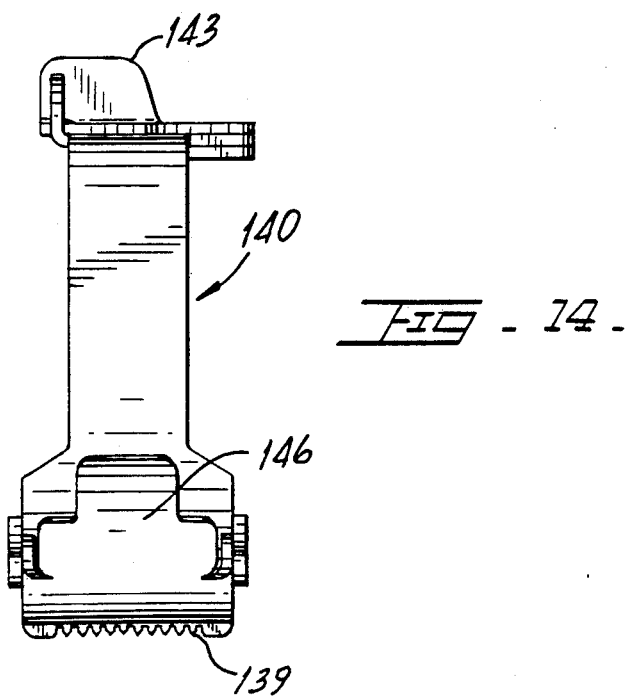
FIG. 14 is an end view of the elongated gripping instrument shown in FIGS. 12 and 13.

Elongated gripping instrument 140 is shown in FIGS. 12 through 14 and it is very similar to gripping instrument 40, described above. It includes elongated lower L-shaped jaw member 144, smaller upper L-shaped member 146, and spring member 147. The main difference being the elongated neck member 145 that permits it to reach deeper layers of tissues. Similarly, mounting assembly 142 is removably and pivotally mounted to frame assembly 20 so that gripping instrument 140 can be directed in any desired angle to exert the desired pulling action on the tissue grabbed. Similarly, member 144 includes several cut-outs 149 at end 144" that receive locking pin 143'. Headed pin 148 also extends downwardly from mounting assembly 142 with cooperative dimensions to permit it, insertion through opening 22. Similarly, serrations 139 are provided as terminations for ends 144' and 146' in order to ensure the effective gripping of the tissues being pulled away.

It is believed the foregoing description conveys the best understanding of the objects and advantages of the present invention. Different embodiments may be made of the inventive concept of this invention. It is to be understood that all matter disclosed herein is to be interpreted merely as illustrative, and not in a limiting sense.

What is claimed is:

1. A retractor used in hernia surgery for separating body parts and tissues from the area being operated on, comprising:
   A. flat frame means having substantially an elliptical shape and including a plurality of through openings around said flat frame means;
   B. at least one gripping instrument means for effectively holding said tissues including gripping means and first mounting means removably and pivotally mounted through one of said openings in said frame means so that said gripping instrument means can be positioned in any desired angle for pulling said tissues away from the area being operated on and said gripping means further including upper and lower jaw means that are urged towards each other by cooperatively biased spring means, and said gripping means being slidably and adjustably inserted through said first mounting means.

2. The retractor set forth in claim 1 further including:
   C. at least one hook instrument means having a hook member with a straight end and a hook end and further having a second mounting means that is removably and pivotally mounted through one of said through openings in said frame means so that said hook instrument means can be positioned in any desired angle for pulling said body parts away from the area being operated on and said hook member being slidably and adjustably inserted through said second mounting means.

3. The retractor set forth in claim 2 further including:
   D. at least one elongated gripping instrument means having elongated gripping means and a third mounting means that is removably and pivotally mounted through one of said through openings in said frame means so that said elongated gripping instrument means can be positioned in any desired angle for pulling said body tissues away from the area being operated on and said elongated gripping means being slidably and adjustably inserted through said third mounting means.

4. The retractor set forth in claim 3 wherein said lower jaw means includes a lower L-shaped jaw member having a longer arm and a smaller arm and said upper jaw means having a cooperative smaller L-shaped upper jaw member having first and second, said first end being normally in touch with said smaller arm, said, spring means so adapted and constructed to cause said smaller arm and said first end to be normally in touch and wherein said upper and lower jaw members may be separated by applying pressure to the second end of said upper jaw member.

5. The retractor set forth in claim 4 wherein said longer arm of said lower L-shaped jaw member includes a plurality of cut-outs and said first mounting means includes latching means for securely holding said first mounting means in place with respect to said lower L-shaped jaw member.

6. The retractor set forth in claim 5 wherein said second mounting means includes lever means hingedly mounted to said second mounting means and including a locking pin perpendicularly mounted thereon and said hook member further including a plurality of openings along said straight end that cooperatively receive said locking pin thereby keeping said second mounting means in place with respect to said hook member.

* * * * *